US009890392B2

(12) United States Patent
Hamada

(10) Patent No.: US 9,890,392 B2
(45) Date of Patent: Feb. 13, 2018

(54) METHOD FOR PREPARING SPECIFIC CELLS OF HUMAN-DERIVED CELLS

(71) Applicant: TRDIGM & CO., LTD., Naha-shi (JP)

(72) Inventor: Katsutomo Hamada

(73) Assignee: TRDIGM & CO., LTD., Naha-shi (JP)

( * ) Notice: Subject to any disclaimer, the term of this patent is extended or adjusted under 35 U.S.C. 154(b) by 90 days.

(21) Appl. No.: 14/434,284

(22) PCT Filed: Feb. 5, 2013

(86) PCT No.: PCT/JP2013/052609
§ 371 (c)(1),
(2) Date: Apr. 8, 2015

(87) PCT Pub. No.: WO2014/122729
PCT Pub. Date: Aug. 14, 2014

(65) Prior Publication Data
US 2015/0259703 A1    Sep. 17, 2015

(51) Int. Cl.
*C12N 5/00* (2006.01)
*C12N 5/02* (2006.01)
*C12N 5/071* (2010.01)
*C12N 15/85* (2006.01)
*C12N 9/12* (2006.01)
*C12N 9/14* (2006.01)
*G01N 33/50* (2006.01)
*C12N 15/11* (2006.01)

(52) U.S. Cl.
CPC .......... *C12N 15/85* (2013.01); *C12N 9/1276* (2013.01); *C12N 9/14* (2013.01); *C12Y 207/07049* (2013.01); *G01N 33/5011* (2013.01); *C12N 15/11* (2013.01); *C12N 2330/10* (2013.01); *C12N 2503/02* (2013.01); *C12N 2510/00* (2013.01); *C12N 2510/04* (2013.01); *C12N 2800/90* (2013.01); *C12Y 306/01003* (2013.01)

(58) Field of Classification Search
CPC .................................................. C12N 15/85
See application file for complete search history.

(56) References Cited

U.S. PATENT DOCUMENTS

2013/0157304 A1    6/2013 Hamada
2014/0212915 A1    7/2014 Hamada

OTHER PUBLICATIONS

Boehm (2005, Mol Cell Biol, 25:6464-6474).*
Akagi, 2003, PNAS, 100:13567-13572.*
Aird (Cold Spring Harbor Perspectives in Medicine, 2012, 2:a006429, pp. 1-13).*
International Search Report dated Mar. 5, 2013 in PCT/JP2013/052609.
Beicheng Sun, et al., "The Minimal Set of Genetic Alterations Required for Conversion of Primary Human Fibroblasts to Cancer Cells in the Subrenal Capsule Assay" Neoplasia, vol. 7, No. 6, Jun. 2005, pp. 585-593.
Michael Thomas, et al., "Cooperation of hTERT, SV40 T Antigen and Oncogenic Ras in Tumorigenesis: A Cell Transplantation Model Using Bovine Adrenocortical Cells" Neoplasia, vol. 4, No. 6, 2002, pp. 493-500.
Beicheng Sun, et al., "Tumorigenic Study on Hepatocytes Coexpressing SV40 With Ras" Molecular Carcinogenesis, vol. 45, No. 4, 2006, pp. 213-219.
Katsutomo Hamada, "Morphological Transformation Caused by a Partial Sequence of U5 Small Nuclear RNA" Molecular Carcinogenesis, vol. 20, 1997, pp. 175-188.
Katsutomo Hamada, et al., "Effect of Transforming RNA on the Synthesis of a Protein with a Secretory Signal Sequence in Vitro" The Journal of Biological Chemistry, vol. 274, No. 22, May 28, 1999, pp. 15786-15796.

* cited by examiner

*Primary Examiner* — Valerie E Bertoglio
(74) *Attorney, Agent, or Firm* — Oblon, McClelland, Maier & Neustadt, L.L.P.

(57) ABSTRACT

A method for preparing neoplastically transformed cells from human-derived cells, including the step of introducing human telomerase catalytic subunit (hTERT) gene, SV40 small T antigen (SV40ST) gene, and an oligonucleotide derived from Alu7 sequence into the human-derived cells. A method for introducing a gene for neoplastically transforming human-derived cells, including incorporating human telomerase catalytic subunit (hTERT) gene, SV40 small T antigen (SV40ST) gene, and an oligonucleotide derived from Alu7 sequence into the same or different vectors, and introducing the genes into human-derived cells therewith. The methods of the present invention can be utilized upon induction of neoplastic transformation to various human normal cells in order to elucidate mechanisms for onset of cancer, so that the method can be effectively utilized in the search of a new drug discovery target molecule.

1 Claim, 3 Drawing Sheets

Figure 1A
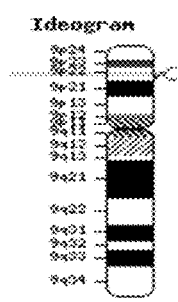
Figure 1C
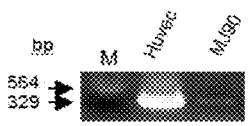
Figure 1B

```
                        SEQUENCE LISTING

<160> NUMBER OF SEQ ID NOS: 4

<210> SEQ ID NO 1
<211> LENGTH: 337
<212> TYPE: DNA
<213> ORGANISM: Homo sapiens

<400> SEQUENCE: 1
gatagcctta gtttgttaag aaattgccag ctgggtgcag cggcttatgc ctgtaatctt      60
agcactttgg gaggccgagg tgggtggatc acctgaagtc aggagtttga aaccagcctg     120
gccaatatgg tgaaacccca tctctaccaa aaatataaaa attagccgga cgtggtggtg     180
ggtgcctgta gtcccagcta ctcgggaggc tgagacagga gaattgcttc aacccgggag     240
gcggaggttg cagtgagccg ggattgtgcc actgcactcc agcctgggca acagcacgag     300
actccgtctc agcaaaaaaa aaaaaaaaaa aaaaaaa                              337

<210> SEQ ID NO 2
<211> LENGTH: 50
<212> TYPE: DNA
<213> ORGANISM: Homo sapiens

<400> SEQUENCE: 2
gggaggctga gacaggagaa ttgcttcaac ccgggaggcg gaggttgcag                 50

<210> SEQ ID NO 3
<211> LENGTH: 20
<212> TYPE: DNA
<213> ORGANISM: Artificial Sequence
<220> FEATURE:
<223> OTHER INFORMATION: primer for Alu7

<400> SEQUENCE: 3
tgggccatgt gattgttata                                                  20

<210> SEQ ID NO 4
<211> LENGTH: 20
<212> TYPE: DNA
<213> ORGANISM: Artificial Sequence
<220> FEATURE:
<223> OTHER INFORMATION: primer for Alu7

<400> SEQUENCE: 4
cctgagacgg agtctcgtgc                                                  20
```

METHOD FOR PREPARING SPECIFIC CELLS OF HUMAN-DERIVED CELLS

TECHNICAL FIELD

The present invention relates to a method for preparing neoplastically transformed cells from human-derived cells. More specifically, the present invention relates to a method for preparing neoplastically transformed cells from human-derived cells using an oligonucleotide derived from Alu7 sequence, cells obtainable by the method, a kit for use in the method, and a method of using the cells in assessment of pharmacologically efficacy of an anticancer agent.

BACKGROUND ART

In general, neoplastic transformation is caused by a mutation in just a single cell as an initiation point so that clonal proliferation is shown to develop benign tumors.

The present inventor has so far reported that a non-coding mRNA having a particular sequence is capable of inducing immortalized rat cells to neoplastically transformed cells (see, Non-Patent Publications 1 and 2). Concretely, the present inventors has found that a particular polypurine sequence in the mRNA is bound with 28S rRNA of the ribosome, whereas the antisense sequence of the polypurine sequence is bound with the Alu portion of 7SL RNA of a signal recognition particle (SRP). These sequences affect both 28S rRNA and 7SL RNA, thereby controlling protein synthesis to transform into neoplastically transformed cells.

In addition, the present inventor has reported that human-derived cells can be transformed by using a short chained RNA (asR70, asR56, and asR46) complementary to ES27 of human 28S rRNA, together with human telomerase catalytic subunit (hTERT) gene and SV40 small T antigen (SV40ST) gene (see, Patent Publication 1). The resulting transformed cells have anchorage-independent proliferative ability, and show chromosomal abnormalities.

PRIOR ART REFERENCES

Patent Publications

Patent Publication 1: Japanese Patent Laid-Open No. 2011-239726

Non-Patent Publications

Non-Patent Publication 1: K. Hamada, "Morphological transformation caused by a partial sequence of U5 small nuclear RNA." *Mol. Carcinog.*, 1997, 20, 175-188
Non-Patent Publication 2: K. Hamada et al, "Effect of Transforming RNA on the Synthesis of a Protein with a Secretory Signal Sequence in Vitro." *J. Biol. Chem.*, 1999, 274(22), 15786-15796

SUMMARY OF THE INVENTION

Problems to be Solved by the Invention

However, the molecular mechanisms underlying the initiation point of neoplastic transformation have not yet been elucidated at present. In addition, when cells transformed with the above-mentioned short chained RNA (asR70, asR46) are transplanted to nude mice, tumor formation is not recognized, so that it is found that the transformation is not sufficient.

An object of the present invention is to provide a method of transforming cells from human-derived cells to neoplastically transformed cells, cells obtainable by the method, a kit for use in the method, and a method of using the cells in assessment of pharmacological efficacy of an anticancer agent, which are free from the problems of safety.

Means to Solve the Problems

The present inventor has considered that high incidences of cancer take place by a first mutation that occurs in genes having high-copy-numbers, and remarked on Alu transcript to carry out intensively studies, and as a result, the present inventor has found that a particular Alu sequence is involved in neoplastic transformation, and the present invention is perfected thereby.

Concretely, the present invention relates to the following [1] to [6]:
[1] a method for preparing neoplastically transformed cells from human-derived cells, including the step of introducing human telomerase catalytic subunit (hTERT) gene, SV40 small T antigen (SV40ST) gene, and an oligonucleotide derived from Alu7 sequence into the human-derived cells;
[2] a method for introducing a gene for neoplastically transforming human-derived cells, including incorporating human telomerase catalytic subunit (hTERT) gene, SV40 small T antigen (SV40ST) gene, and an oligonucleotide derived from Alu7 sequence into the same or different vectors, and introducing the genes into human-derived cells therewith;
[3] neoplastically transformed cells from human-derived cells, obtainable by the method as defined in the above [1];
[4] a kit for use in the method as defined in the above [1] or [2], containing human telomerase catalytic subunit (hTERT) gene, SV40 small T antigen (SV40ST) gene, and an oligonucleotide derived from Alu7 sequence;
[5] a method for screening an anticancer agent, characterized by culturing neoplastically transformed cells from human-derived cells obtained by the method as defined in the above [1] in the presence or absence of a candidate compound, and judging that the candidate compound has a high possibility of having an action as an anticancer agent in a case where the degree of the neoplastic transformation of the human-derived cells in the presence of the candidate compound is inhibited, as compared to the neoplastic transformation of the human-derived cells in the absence thereof; and
[6] a method for screening an anticancer agent, characterized by culturing human-derived cells introduced with a gene by the method as defined in the above [2] in the presence or absence of a candidate compound, and judging that the candidate compound has a high possibility of having an action as an anticancer agent in a case where the degree of the neoplastic transformation of the human-derived cells in the presence of the candidate compound is inhibited, as compared to the neoplastic transformation of the human-derived cells in the absence thereof.

Effects of the Invention

According to the method for preparing neoplastically transformed cells from human-derived cells of the present invention, the human-derived cells can be more safely induced to neoplastically transformed cells having a potent neoplastically transforming character.

BRIEF DESCRIPTION OF THE DRAWINGS

FIG. 1 is a set of drawings showing the loci of Alu7 oligonucleotide and Alu7i oligonucleotide, wherein FIG. 1-*a* is a view showing an alignment of Alu7 on human chromosome 9, FIG. 1-b is a view mapping Alu7 oligonucleotide and Alu7i oligonucleotide on human chromosome 9 (nucleotides 17164352-17164720), and FIG. 1-c is a view showing that Alu7 is contained in cDNA prepared from HUVEC cells and MJ90 cells.

Figure 2:
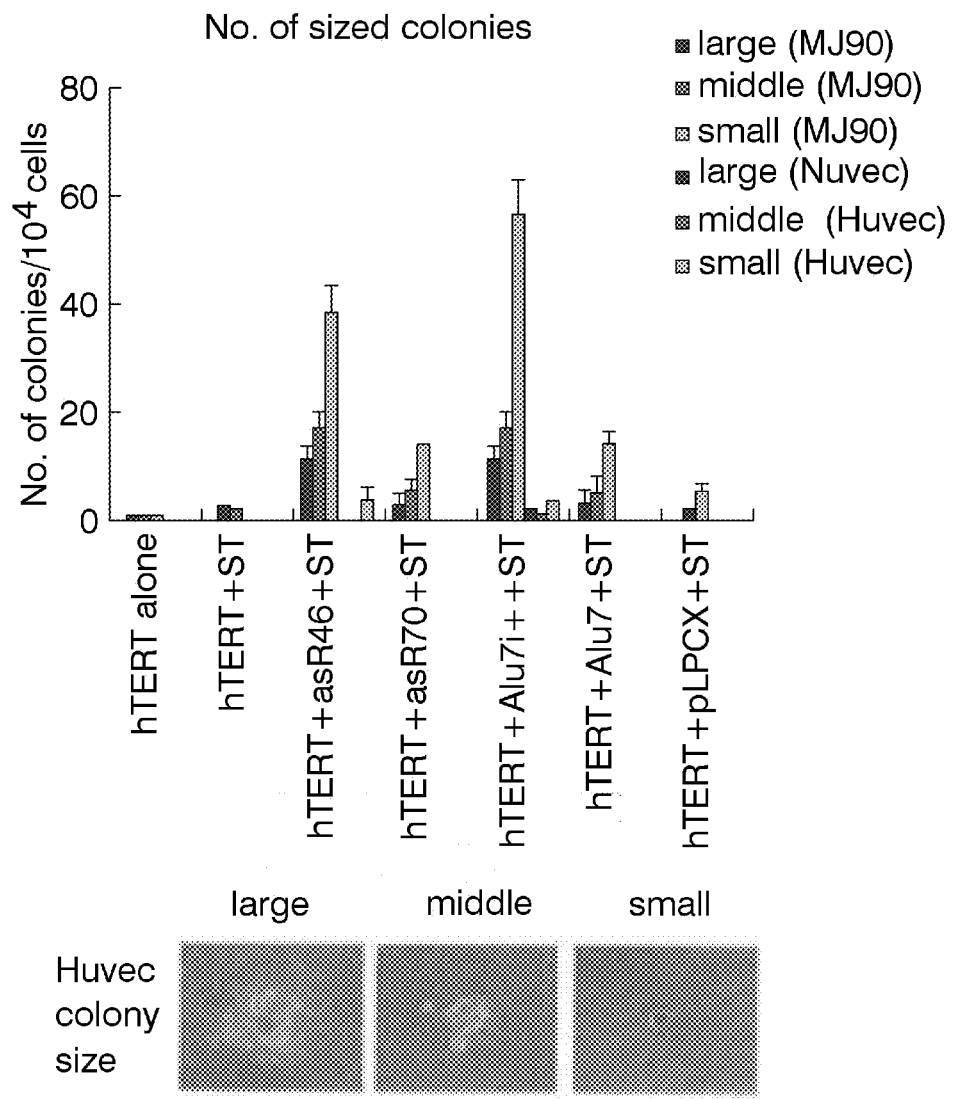

FIG. 2 is a set of drawings showing colony formation in soft agar media. Photographs show, starting from the left panel, general examples of large colonies, middle colonies, and small colonies, respectively.

Figure 3:
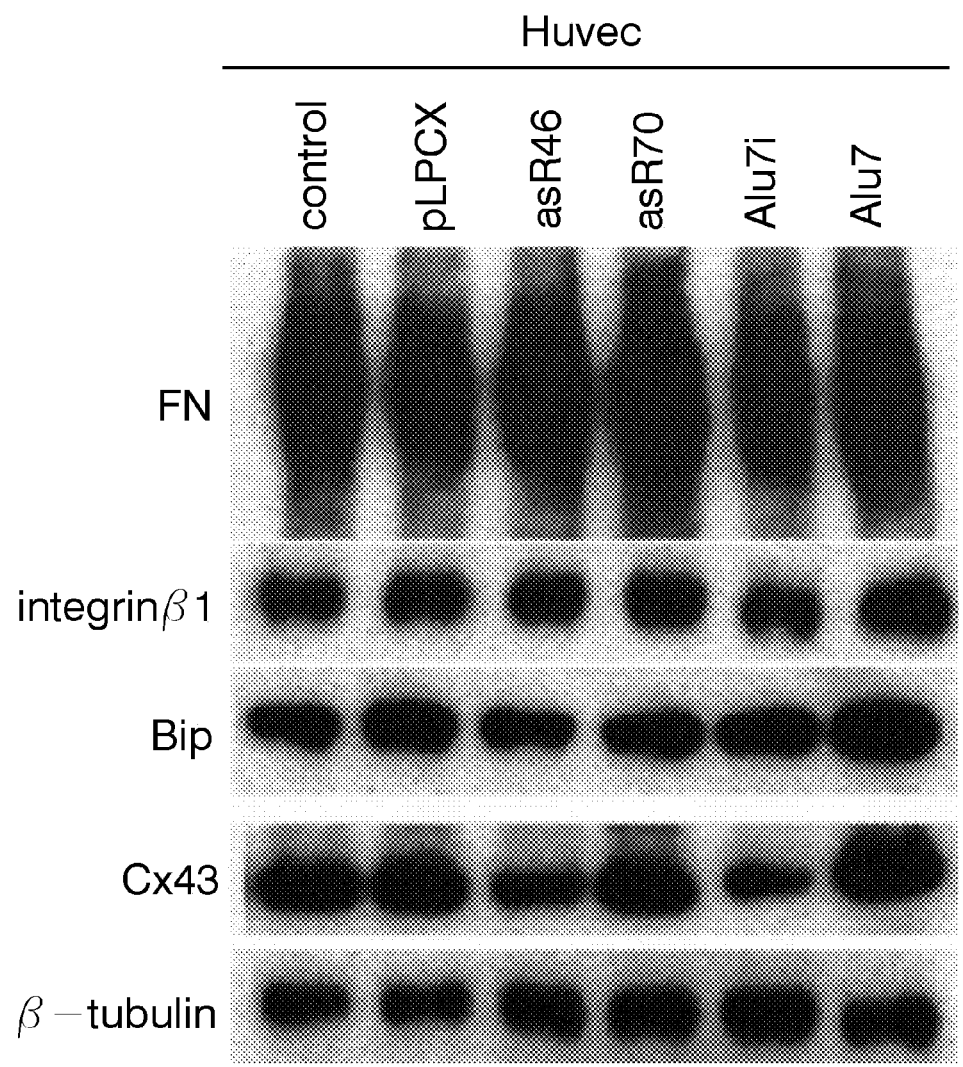

FIG. 3 is a view showing the results of induction of the endoplasmic reticulum response stress.

MODES FOR CARRYING OUT THE INVENTION

The method for preparing neoplastically transformed cells from human-derived cells of the present invention includes the step of introducing human telomerase catalytic subunit (hTERT) gene and SV40 small T antigen (SV40ST) gene into the human-derived cells, wherein the method has a great feature that an oligonucleotide derived from Alu7 sequence is used together therewith.

The Alu family exists in about 1,000,000 copies that are appropriately 300 base pairs in length, in the human genome, and is generally transcribed to intranuclear RNA or the like with RNA polymerase III. As a result of preparing cDNA of various Alu transcripts from Hela cells, and obtaining and analyzing Alu7 clone of 337 bases in length, the present inventor has found that the Alu7 sequence does not contain a transcription initiation site or consensus split promoters by RNA polymerase III, so that the sequence is deduced to be an incomplete transcript by RNA polymerase II. In view of the above, when this Alu7 sequence is used together with hTERT and SV40ST, it has been surprisingly found that the sequence transforms human-derived cells. The resulting transformed cells have anchorage-independent proliferative ability, and chromosomes show abnormalities, thereby making it possible to introduce hTERT and SV40ST by the use of an oligonucleotide derived from Alu7 sequence, whereby suggesting that the human-derived cells can be transformed into neoplastically transformed cells (neoplastically transformed cells). The degree of "neoplastic transformation" or "neoplastic transformation" of human-derived cells as used herein means a degree of immortalization and proliferation of the cells, or a level showing a state of cells that are different from normal cells.

The method for preparing neoplastically transformed cells (neoplastically transformed cells) from human-derived cells of the present invention includes the step of introducing human telomerase catalytic subunit (hTERT) gene, SV40 small T antigen (SV40ST) gene, and an oligonucleotide derived from Alu7 sequence into the human-derived cells.

The term "gene" as used herein refers to a factor that carries the heredity information of an organism, which is meant to be used to include DNA and RNA. Also, the term "oligonucleotide" is meant to be used to include DNA and RNA.

The human telomerase catalytic subunit (hTERT) gene is not particularly limited, and includes those known in the field of art. The telomerase is an enzyme that maintains a telomeric length by being antagonistic to the shortening of the telomeric length by cell division. The telomerase contains as constituents RNA used as a template of the telomeric sequence, and a reverse transcriptase, and this reverse transcriptase moiety is hTERT.

The SV40 small T antigen (SV40ST) gene is not particularly limited, and includes those known in the field of art. The SV40 (Simian virus 40) is a virus belonging to Polyomavirus, and is separated from Rhesus monkey kidney cells, and this virus produces a large T antigen and a small T antigen as early stage proteins, at an early infection stage to cells (before DNA synthesis takes place). In the present invention, the small T antigen is used as an antigenic virus.

The oligonucleotide derived from the Alu7 sequence includes an oligonucleotide containing the nucleotide sequence shown in SEQ ID NO: 1, and an oligonucleotide containing the nucleotide sequence shown in SEQ ID NO: 2. Among them, an oligonucleotide essentially consisting of the nucleotide sequence shown in SEQ ID NO: 1, and an oligonucleotide essentially consisting of the nucleotide sequence shown in SEQ ID NO: 2 are preferred, and an oligonucleotide consisting of the nucleotide sequence shown in SEQ ID NO: 1, and an oligonucleotide consisting of the nucleotide sequence shown in SEQ ID NO: 2 are more preferred.

In addition, in the present invention, oligonucleotides having deletion, addition, insertion or substitution of one or more nucleotides in the above nucleotide sequence are preferably used as the above oligonucleotide. Concretely, the oligonucleotide includes oligonucleotides having homology of at least 70% or more, preferably 80% or more, more preferably 90% or more, and even more preferably 95% or more, to the oligonucleotide shown in the above nucleotide sequence. Also, the nucleotide length is preferably from 30 to 500, more preferably from 40 to 425, even more preferably from 45 to 375, and even more preferably from 48 to 355. The oligonucleotide as described above exhibits similar effects (neoplastic transformation of human-derived cells) to the cases of using the oligonucleotide consisting of the nucleotide sequence shown in SEQ ID NO: 1 or the oligonucleotide consisting of the nucleotide sequence shown in SEQ ID NO: 2. Here, the term homology as used herein can be obtained by, for example, using a search program BLAST in which an algorithm developed by Altschul et al. (*The Journal of Molecular Biology*, 215, 403-410 (1990)) is employed.

A view of mapping an oligonucleotide consisting of the nucleotide sequence shown in SEQ ID NO: 1 and an oligonucleotide consisting of the nucleotide sequence shown in SEQ ID NO: 2 on human chromosome 9 is shown in FIG. 1-b. The oligonucleotide consisting of the nucleotide sequence shown in SEQ ID NO: 1 has 337 nucleotides in length, which corresponds to positions 17164384 to Ser. No. 17/164,720 nucleotides on chromosome 9 (hereinafter also referred to as Alu7). The oligonucleotide consisting of the nucleotide sequence shown in SEQ ID NO: 2 is a part of Alu7 (50 nucleotides in length), and corresponds to positions 17164587 to Ser. No. 17/164,636 on chromosome 9 (hereinafter also referred to as Alu7i).

The method for synthesizing an oligonucleotide derived from Alu7 sequence is not particularly limited, and a phosphoramidite method, a phosphorothioate method, a phosphotriester method or the like, using a known oligonucleotide synthesizer can be employed.

The gene and the oligonucleotide mentioned above may be a modified or substituted product in accordance with a known method within the range that would not markedly lower its activity, in order to increase stability and affinity to the cells. For example, the gene and the oligonucleotide can be also used in the form of a derivative formed by substituting a phosphate group, or a hydroxyl group or hydroxyl groups of a ribose moiety, with another stable group.

The human-derived cells into which the gene and the oligonucleotide described above are introduced are not particularly limited, and include human fibroblast cells, human endothelial cells, human epithelial cells, and the like. The derivations of the above-mentioned cells or tissues are not particularly limited.

The method of introducing the gene and the oligonucleotide mentioned above into human-derived cells is not particularly limited. For example, a product obtained by incorporating the gene and the oligonucleotide mentioned above into any vector can be used.

It is preferable that the vector is self-replicable in a host cell, and further contains, in addition to the gene and the oligonucleotide mentioned above, a promoter and a transcription termination sequence. In addition, the vector may contain a gene controlling a promoter. Here, the promoter is not particularly limited so long as the gene and the oligonucleotide mentioned above can be expressed in a host cell.

The preferred vector usable in the present invention includes, for example, adenoviral vector, Vaccinia virus vector, retrovirus vector and the like.

The gene and the oligonucleotide mentioned above may be introduced at the same time, collectively or individually, and they may each be introduced in a combination of different timing or individually, and it is preferable that the hTERT gene and SV40ST gene are introduced, and an oligonucleotide derived from Alu7 sequence is then introduced. The gene and the oligonucleotide mentioned above may be incorporated into separate vectors and used, or may be incorporated into the identical vector and used. In a case where the gene and the oligonucleotide incorporated into separate vectors are used, for example, those in which hTERT gene is incorporated into pBABE vector, those in which SV40ST gene is incorporated into pLHCX vector, and those in which an oligonucleotide derived from Alu7 sequence is incorporated into pLHCX vector can be used. Also, in a case where the gene and the oligonucleotide incorporated into the identical vector are used, a preferred vector includes retroviral vector, and the locations of the gene and the oligonucleotide mentioned above in the vector are not particularly limited, and for example, the gene and the oligonucleotide are located between a promoter and a transcription termination sequence, in the order of hTERT gene, SV40ST gene, and the oligonucleotide derived from Alu7 sequence, starting from the promoter side.

The method for introducing a vector includes an electroporation method, a calcium phosphate method, a lipofection method and the like.

In addition, the vector may be introduced by preparing a vector obtained by further incorporating viral DNA for infection to the introduced cells into the above-mentioned vector, thereby infecting human-derived cells with the vector-introduced virus. The virus for infection includes adenovirus, adeno-associated virus, retrovirus, and the like.

Here, the method of constructing the vector, a concrete method of using the vector, and the like may be referred to, for example, textbooks such as Sambrook, J., et. al., *Molecular Cloning: A Laboratory Manual;* $2^{nd}$ Ed., Cold Spring Harbor Laboratory, Cold Spring Harbor. N.Y., 1989.

Thus, hTERT gene, SV40ST gene, and an oligonucleotide derived from Alu7 sequence can be introduced into human-derived cells. The cells obtained are formed into transformed cells which express a protein encoded by hTERT and SV40ST. Therefore, the present invention provides cells obtainable by introduction of the hTERT gene, the SV40ST gene, and the oligonucleotide derived from Alu7 sequence. The cells may be cultured under conditions appropriate for the cells to repeat population doubling, and screened with a known agent. Here, in the present invention, those obtained by introducing SV40ST gene and an oligonucleotide derived from Alu7 sequence into hTERT immortalized cells into which hTERT gene is already incorporated are also embraced within the scope of the present invention. As to the condition of human-derived cells in which transformation is induced by hTERT gene, SV40ST gene, and an oligonucleotide derived from Alu7 sequence, the cell morphologies can be confirmed with a phase contrast microscope.

In addition, in the present invention, human-derived cells can be neoplastically transformed by using hTERT gene, SV40ST gene, and an oligonucleotide derived from Alu7 sequence in combination, so that a kit containing hTERT gene, SV40ST gene, and an oligonucleotide derived from Alu7 sequence can be used for the transformation of human-derived cells. The present invention also provides a kit containing hTERT gene, SV40ST gene, and an oligonucleotide derived from Alu7 sequence.

Furthermore, the neoplastic transformation of human-derived cells is facilitated by introducing hTERT gene, SV40ST gene, and an oligonucleotide derived from Alu7 sequence in combination, and a degree of transformation is at a certain level, so that human-derived cells that are neoplastically transformed using hTERT gene, SV40ST gene, and an oligonucleotide derived from Alu7 sequence, or human-derived cells into which hTERT gene, SV40ST gene, and an oligonucleotide derived from Alu7 sequence are introduced, can be used in screening an anticancer agent. Therefore, the present invention provides a method of screening an anticancer agent. The above-mentioned method is an in vitro assessment in the human system, assumption to in vivo assessment is facilitated, so that an effective substance can be found more conveniently and quickly.

A concrete method includes:

an embodiment of culturing neoplastically transformed cells from human-derived cells obtained by introducing the above genes in the presence or absence of a candidate compound, and judging that the candidate compound has a high possibility of having an action as an anticancer agent in a case where a degree of the neoplastic transformation of the human-derived cells in the presence of the candidate compound is inhibited, as compared to the neoplastic transformation of the human-derived cells in the absence thereof (Embodiment 1); and an embodiment of culturing human-derived cells into which the above genes are introduced in the presence or absence of a candidate compound, and judging that the candidate compound has a high possibility of having an action as an anticancer agent in a case where a degree of the neoplastic transformation of the human-derived cells in the presence of the candidate compound is inhibited, as compared to the neoplastic transformation of the human-derived cells in the absence thereof (Embodiment 2).

In Embodiment 1 and Embodiment 2, the conditions for culturing the cells in the presence or absence of the candidate compound can be carried out in the same manner according to known conditions when the cells are cultured before the above genes are introduced, except for the presence or absence of the candidate compound, and are not particularly limited.

In Embodiment 1, when it is judged that the candidate compound has a high possibility of having an action as an anticancer agent, in a case, for example, where a part of the cells cultured in the presence of the candidate compound is found to undergo changes such as transformed morphological losses, induction of apoptosis, and anchorage-independent losses, as compared to the cells cultured in the absence thereof, a candidate compound to which the cells are contacted has an action as an anticancer agent, so that the candidate compound can be judged to have an effect of diminishing neoplastic transformation.

In Embodiment 2, when it is judged that the candidate compound has a high possibility of having an action as an anticancer agent, in a case, for example, where a part of the cells cultured in the presence of the candidate compound is found to have a smaller degree of population doubling and change in cell morphologies, as compared to the cells cultured in the absence thereof, a candidate compound to which the cells are contacted has an action as an anticancer agent, so that the candidate compound can be judged to have an effect of diminishing neoplastic transformation.

EXAMPLES

The present invention will be explained hereinbelow on the basis of Examples, without intending to limit the present invention to these Examples and the like. Here, hTERT gene was obtained from Dr. F. Ishikawa or addgene 1774, SV40ST gene was obtained from JCRB gene bank (pMTI0D), and used. The oligonucleotide derived from Alu7 sequence was obtained with a kit manufactured by Clontech. In addition, HUVEC (human umbilical vein endothelial cells) were obtained from JCRB bank, and MJ90 (fibroblasts derived from human skin) were obtained from J. R. Smith, and used.

<Reference Example 1> Locations of Alu7 and Alu7i

Using HUVEC (human umbilical vein endothelial cells) extract, or MJ90 (fibroblasts derived from human skin) extract, RT-PCR was carried out with the following Alu7-specific primers. The results are shown in FIG. 1-c.

```
                                          (SEQ ID NO: 3)
  forward: 5'-tgggccatgtgattgttata-3'

(SEQ ID NO: 4)
  reverse: 5'-cctgagacggagtctcgtgc-3'
```

As a result, it can be seen that both of the extracts contain Alu7.

<Example 1> Morphologies of Transformed Cells, Neoplastically Transforming Character Colony formation tests were conducted in a soft agar medium for MJ90 cells or HUVEC cells, transformed with hTERT, Alu7 or Alu7i, and SV40ST.

Concretely, the transformed cells prepared in the following manner were used. First, Alu7 or Alu7i was inserted into pLPCX (manufactured by Clontech) cleaved with HindIII-BamHI, to prepare a vector (pLPCX-Alu7, pLPCX-Alu7i). Also, an SV40ST fragment amplified by PCR was inserted into pLHCX (manufactured by Clontech) to prepare a vector (pLHCX-ST). As the plasmids for hTERT expression, pcD-NAhTERTn2 (provided by Dr. F. Ishikawa) and pBABE-neo-hTERT (Addgene plasmid 1774) were used. Next, 293T cells (obtained from Riken Cell Bank) were transfected with pLPCX-Alu7, pLPCX-Alu7i and pLHCX-ST, together with a retrovirus packaging plasmid pCL-10A1 (manufactured by Imgenex), the virus was then collected, and thereafter the MJ90 cells or the HUVEC cells were infected with the virus.

On the other hand, in a case where pcDNAhTERTn2 was used, the MJ90 cells or the HUVEC cells were transfected with lipofectamine 2000. For example, in a case where the cells were transfected with all of hTERT, Alu7 or Alu7i, and SV40ST, the MJ90 cells or the HUVEC cells introduced with hTERT were transfected with Alu7 or Alu7i, and SV40ST in accordance with the method described above. The cells obtained were subjected to drug screening to select the cells having a life span longer than the parental cells to be used in the experiment.

The resulting cells were cultured in a soft agar medium, and subjected to colony formation test (n=3). In a case where colony formation was found, the sizes of the colonies were classified into "L (large, a size of 10 times or more of the cells)," "M (middle, a size of from 5 to 9 times or so of the cells)," and "S (small, a size of 3 or 4 times or so of the cells," and the number of colonies were counted, respectively. The results are shown in FIG. 2. Here, for the sake of comparison, cells introduced with asR70 or asR46 were prepared in accordance with the method described in Japanese Patent Laid-Open No. 2011-239726, and experimentations were conducted in the same manner.

As a result, the cells transformed with hTERT, Alu7 or Alu7i, and SV40ST were confirmed to form colonies in the soft agar, and it can be seen that all the cells have anchorage-independent proliferative ability and are neoplastically transformed. Among them, cells introduced with Alu7i form a larger number of colonies than the cells introduced with asR70, asR46, or Alu7, thereby suggesting a high neoplastic transformation efficiency.

<Example 2> Induction of Endoplasmic Reticulum Stress Response in Transformed Cells HUVEC cells transformed in the same manner as in Example 1 were confirmed for expression of substances showing endoplasmic reticulum stress responses. In addition, for the sake of comparison, cells introduced with asR70 or asR46 were prepared in accordance with the method described in Japanese Patent Laid-Open No. 2011-239726, and experimentations were conducted in the same manner.

Concretely, in accordance with a pulse label immunoprecipitation method using $^{35}$S-methionine, expression levels of fibronectin (FN) of extracellular matrix, integrin beta 1 (integrin β1) membrane-permeable receptor, endoplasmic reticulum-localized chaperone Bip, and gap junctional protein connexin 43 (Cx 43) were measured for each of the cells. Here, the expression level of β-tubulin was used as the control. The results are shown in FIG. 3.

It could be seen from FIG. 3 that expression of Cx 43 was markedly reduced in cells asR46 and cells Alu7i. On the other hand, expression of FN and integrin β1 showed a tendency similar to signal-independent β-tubulin, so that hardly any changes were found. The FN and integrin β1 had a high productivity in the cells, so that a change was not found, but a change in expression levels of Cx43 was found, thereby suggesting that synthesis of Cx43 is inhibited in ribosomes of cells asR46 and cells Alu7i.

<Example 3> Screening of Anti-Cancer Agent

Cells introduced with hTERT, SV40ST, and an oligonucleotide derived from Alu7 sequence are cultured in a cell culture equipment, and a solution prepared by dissolving a candidate compound in a solvent is added thereto, and the cells are further cultured. On the other hand, as a control, a group without addition of a candidate compound is also set.

Using the group without addition of a candidate compound as the control, in a case where changes such as transformed morphological losses of cells, induction of apoptosis, anchorage-independent proliferation losses are found more than the group without addition, the candidate compound added to the cells can be judged to have a high possibility of having an action as an anti-cancer agent.

INDUSTRIALLY APPLICABILITY

The method for preparing neoplastically transformed cells from human-derived cells of the present invention can be utilized upon induction of neoplastic transformation from various human normal cells in order to elucidate mechanisms for onset of cancer, so that the method can be effectively utilized in the search of a new drug discovery target molecule.

SEQUENCE LISTING FREE TEXT

SEQ ID NO: 1 of the Sequence Listing is an oligonucleotide Alu7 derived from Alu7 sequence.
SEQ ID NO: 2 of the Sequence Listing is an oligonucleotide Alu7i derived from Alu7 sequence.
SEQ ID NO: 3 of the Sequence Listing is a primer for Alu7.
SEQ ID NO: 4 of the Sequence Listing is a primer for Alu7.

The invention claimed is:

1. A method for preparing neoplastically transformed cells from human fibroblast cells or HUVEC cells, the method comprising:
   introducing a nucleic acid encoding a human telomerase catalytic subunit (hTERT), a nucleic acid encoding an SV40 small T antigen (SV40ST), and a nucleic acid derived from an Alu7 sequence into the same vector or different vectors and introducing the vector or the vectors into the human fibroblast cells or HUVEC cells,
   wherein the nucleic acid derived from the Alu7 sequence is a nucleic acid comprising the nucleotide sequence of SEQ ID NO: 1 or a nucleic acid comprising the nucleotide sequence of SEQ ID NO: 2,
   wherein the vector or the vectors comprise a promoter operatively linked to the nucleic acid encoding hTERT and the nucleic acid encoding SV40ST, and to the nucleic acid derived from the Alu7 sequence,
   wherein the neoplastically transformed cells have anchorage-independent proliferative ability and chromosomes show abnormalities, and
   wherein expression of the nucleic acids results in neoplastic transformation.

* * * * *